(12) United States Patent
Wahlstrand (10) Patent No.: US 7,650,192 B2
(45) Date of Patent: Jan. 19, 2010

(54) PASSIVE CHARGE OF IMPLANTABLE MEDICAL DEVICE UTILIZING EXTERNAL POWER SOURCE AND METHOD

(75) Inventor: Carl D. Wahlstrand, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 483 days.

(21) Appl. No.: 11/414,136

(22) Filed: Apr. 28, 2006

(65) Prior Publication Data

US 2007/0129767 A1 Jun. 7, 2007

Related U.S. Application Data

(60) Provisional application No. 60/742,043, filed on Dec. 2, 2005.

(51) Int. Cl.
*A61N 1/378* (2006.01)
(52) U.S. Cl. ........................................ 607/61
(58) Field of Classification Search ................ 607/30, 607/31, 33, 60, 61
See application file for complete search history.

(56) References Cited

U.S. PATENT DOCUMENTS

| | | | |
|---|---|---|---|
| 5,948,006 A | 9/1999 | Mann | |
| 6,047,214 A | 4/2000 | Mueller et al. | |
| 6,212,430 B1 | 4/2001 | Kung | |
| 6,275,737 B1 | 8/2001 | Mann | |
| 6,345,203 B1 | 2/2002 | Mueller et al. | |
| 6,366,817 B1 | 4/2002 | Kung | |
| 6,400,991 B1 | 6/2002 | Kung | |
| 7,158,021 B2 * | 1/2007 | Hammett | 340/500 |
| 2003/0078634 A1 | 4/2003 | Schulman et al. | |
| 2004/0098068 A1 | 5/2004 | Carbunaru et al. | |
| 2004/0212344 A1 | 10/2004 | Tamura et al. | |
| 2005/0075694 A1 | 4/2005 | Schmeling et al. | |
| 2005/0131495 A1 | 6/2005 | Parramon et al. | |
| 2005/0137644 A1 | 6/2005 | Bojeva et al. | |

FOREIGN PATENT DOCUMENTS

| | | |
|---|---|---|
| WO | WO 00/66221 | 11/2000 |
| WO | WO 03/039652 A2 | 5/2003 |

OTHER PUBLICATIONS

International Search report for PCT/US2006/045458.

* cited by examiner

*Primary Examiner*—Carl H Layno
*Assistant Examiner*—Brian T Gedeon
(74) *Attorney, Agent, or Firm*—IPLM Group, P.A.

(57) ABSTRACT

External power source for an implantable medical device implanted in a patient, the implantable medical device having a secondary coil operatively coupled to therapeutic componentry and method therefore. A modulation circuit is operatively coupled to a power source. A plurality of primary coils are operatively coupled to the modulation circuitry and physically associated with an article into which the patient may come into proximity. The modulation circuit drives at least one of the plurality of primary coils. A sensor is coupled to modulation circuit and is adapted to sense proximity of a component related to the implantable medical device. The modulation circuit commences operation to drive at least one of the plurality of primary coils when the sensor senses proximity with the component related to the implantable medical device.

24 Claims, 7 Drawing Sheets

PASSIVE CHARGE OF IMPLANTABLE MEDICAL DEVICE UTILIZING EXTERNAL POWER SOURCE AND METHOD

RELATED APPLICATION

This application claims priority to provisional U.S. Application Ser. No. 60/742,043, filed Dec. 2, 2005.

FIELD OF THE INVENTION

This invention relates to implantable medical devices and, in particular, to energy transfer devices, systems and methods for implantable medical devices.

BACKGROUND OF THE INVENTION

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Of course, it is recognized that other implantable medical devices are envisioned which utilize energy delivered or transferred from an external device.

A common element in all of these implantable medical devices is the need for electrical power in the implanted medical device. The implanted medical device requires electrical power to perform its therapeutic function whether it be driving an electrical infusion pump, providing an electrical neurostimulation pulse or providing an electrical cardiac stimulation pulse. This electrical power is derived from a power source.

In some implantable medical devices electrical power can be transcutaneously transferred through the use of inductive coupling. Such electrical power or energy can optionally be stored in a rechargeable battery. In this form, an internal power source, such as a battery, can be used for direct electrical power to the implanted medical device. When the battery has expended, or nearly expended, its capacity, the battery can be recharged transcutaneously, via inductive coupling from an external power source temporarily positioned on the surface of the skin.

While many devices and techniques have been developed to provide transcutaneous energy transfer in order to power an implantable medical device and/or charge or recharge a battery associated with an implantable medical device, external chargers associated with such devices are sometimes cumbersome and generally require the patient to take some overt step in order to associate an external charger in proximity with an internal, secondary coil associated with the implanted medical device and to initiate steps and/or procedures to accomplish a transcutaneous energy transfer in order to charge or recharge the implanted medical device. In some cases, this may require the patient to consciously remain in contact with or in the proximity of the external charging device. Such charging techniques and equipment tend to limit the flexibility and/or mobility of the patient having an implanted medical device while the device is charging.

U.S. Patent Application No. US 2003/0078634 (A1), Schulman et al, Full-Body Charger For Battery-Powered Patient Implantable Device, attempts to solve the problem of a patient having multiple implanted devices to be recharged. Schulman et al '634 discloses a full-body charger for charging one or more battery-powered devices wherein such devices are configured for implanting beneath a patient's skin for the purpose of tissue, e.g., nerve or muscle, stimulation and/or parameter monitoring and/or data communication. A support structure, typically chair-shaped or bed-shaped, capable of supporting a patient's body while providing a magnetic field to one or more of the implanted devices using one or more coils mounted within for providing power to the implanted devices. As a result, a single, generally sequential, charging cycle can charge all of the implanted devices and thus minimize the charge time requirements for a patient and accordingly improve the patient's lifestyle.

U.S. Pat. No. 6,212,430, Kung, Electromagnetic Field Source With Detection of Position of Secondary Coil In Relation To Multiple Secondary Coils, attempts to locate a secondary coil associated with a particular implanted medical device. Kung discloses an electromagnetic field source for providing electromagnetic energy to a secondary coil, including two or more primary coils that each carry a time-varying current to produce an electromagnetic field, and a controller that selectively provides current to one or more primary coils based on their position with respect to the secondary coil. The secondary coil may be implanted in a human recipient and used to provide power for the operation of a medical device, such as an artificial heart or ventricular assist device. The primary coils may be housed in furniture. For example, they may be housed in a bed mattress or mattress pad on which the recipient rests, or in a blanket for covering the recipient. The controller includes a proximity detector that identifies those primary coils that are closest to the secondary coil, and a current director that, responsive to the proximity detector, selectively direct time-varying current though the closest primary coils.

BRIEF SUMMARY OF THE INVENTION

While the above mentioned devices provide some degree of enablement to either a patient having a plurality of implanted devices to be powered/charged or having an implanted device without a specific location, these devices do not allow the patient to go normal daily activities without thinking about the charging process. In each instance above, the patient must still either go to the support structure of Schulman et al or to the furniture of Kung and initiate the charging process. This, of course, is an interruption in the daily activities of the patient and requires the patient to remember to charge the implanted medical devices at regular intervals to prevent the implanted medical device from becoming discharged.

The present invention provides an external power source and method that is passively initiated. The patient having the implanted medical device need not take any overt action to initiate the charging process. A plurality of primary coils are used, as in the Schulman et al and Kung devices above, however, one or more of these primary coils are automatically activated by proximity to a component associated with the implanted medical device. When the primary coils are physically associated with an article into which the patient may commonly come into proximity, the automatic activation provides a passive charging system that takes no overt action on the part of the patient. This literally frees the patient to go about normal daily activities without regard to charging the implanted medical device and provides the patient with a new sense of freedom.

In an embodiment, the present invention provides an external power source for an implantable medical device implanted in a patient, the implantable medical device having a secondary coil operatively coupled to therapeutic componentry. A modulation circuit is operatively coupled to a power source. A plurality of primary coils are operatively coupled to the modulation circuitry and physically associated with an article into which the patient may come into proximity. The modulation circuit drives at least one of the plurality of primary coils. A sensor is coupled to modulation circuit and is adapted to sense proximity of a component related to the implantable medical device. The modulation circuit commences operation to drive at least one of the plurality of primary coils when the sensor senses proximity with the component related to the implantable medical device.

In an embodiment, the modulation circuit ceases operation to drive at least one of the plurality of primary coils when the sensor ceases to sense proximity with the component related to the implantable medical device.

In an embodiment, the sensor is a pressure sensor and the proximity is sensed through weight of the patient on the article.

In an embodiment, the sensor is a temperature sensor and the proximity is sensed through heat of the patient in proximity to the article.

In an embodiment, the sensor is a metal detector and the proximity is sensed through proximity to the implantable medical device.

In an embodiment, the present invention provides a method of externally powering an implantable medical device implanted in a patient, the implantable medical device having a secondary coil operatively coupled to therapeutic componentry. A plurality of primary coils are physically associated with an article into which the patient may come into proximity. At least one of the plurality of primary coils are modulated. Proximity of a component related to the implantable medical device is sensed. Driving of at least one of the plurality of primary coils is commenced when proximity with the component related to the implantable medical device is sensed.

In an embodiment, driving of at least one of the plurality of primary coils is ceased when proximity with the component related to the implantable medical device is not sensed.

In an embodiment, a pressure through weight of the patient on the article is sensed.

In an embodiment, heat of the patient in proximity to the article is sensed.

In an embodiment, metal through proximity to the implantable medical device is sensed.

In an embodiment, a coil selection circuit is operatively coupled to the plurality of primary coils and to the modulation circuit, the coil section circuit determining which of the plurality of primary coils are in closest proximity to the secondary coil of the implantable medical device, the modulation circuit driving those of the plurality of primary coils selected by the coil selection circuit.

In an embodiment, the implantable medical device has a rechargeable power source operatively coupled to the therapeutic componentry wherein the external power source recharges the rechargeable power through the secondary coil when driven by at least one of the plurality of primary coils.

In an embodiment, the article is an article with which the patient routinely comes into proximity.

In an embodiment, the article is a piece of furniture routinely used by the patient.

In an embodiment, the article is a component of bedding utilized by the patient.

In an embodiment, the article is a component of bedding selected from a group consisting of a mattress, mattress pad, sheet, blanket and pillow.

In an embodiment, the article is an article of clothing worn by the patient.

DETAILED DESCRIPTION OF THE INVENTION

The entire content of provisional U.S. Application Ser. No. 60/742,043, filed Dec. 2, 2005, is hereby incorporated by reference.

Passive charging or recharging refers to devices and methods that allow patients to charge or recharge implanted or external medical devices during their normal daily activities.

The passive recharging devices and methods described below allow patients to recharge their active medical devices without changing any of their daily activities. These devices may allow patients to recharge while sleeping, sitting in a chair, or walking their dog. These devices will also enable patients that would have a hard time charging a device because of its implant location to charge their devices without issues. Passive rechargers also solve the problem of frequency of patient interaction.

An external power source may be used to power or charge external or implanted medical devices placed anywhere on the body of the patient although some embodiments may be designed for specific body locations. The external power source provides form factors and other features allowing the patient to charge or recharge their medical device with no changes or minimal changes to his or her daily routines.

It is to be recognized and understood that although the focus is on passive charging that conventional charging or recharging systems, including those discussed above in the Background section of this document could be in certain circumstances, e.g., when the patient is traveling or otherwise unable to benefit from the passive system described.

In an embodiment, the external power source of the passive charging system can be semi-passive, i.e., devices and methods that fall within the normal daily activities of the patient but that, nevertheless, the patient must actively address at some level. For example, a passive charge external power source could be built into or otherwise associated with a shirt. The patient would need to wear the shirt but wearing a shirt generally would fall within normal everyday activity. Such an external charger is ambulatory and generally powered by batteries. The batteries associated with the external power source can easily be recharged conventionally by plugging into a conventional power source, plug, or by utilizing a special cradle which itself is plugged into a conventional power source. In an embodiment, the external power source is removable from the clothing, e.g., shirt, to facilitate laundry.

In general, clothes that may be used to house a passive external power source can include a vest holding an external power source for charging a medical device located in or around the area of the abdomen. A jacket may be used to charge devices located in or around the area of the abdomen or the arms. Pants may be used to charge devices located in or around the groin area or the legs. Shorts may be used to charge devices located in or around the groin area or the buttocks. An arm band may be used to charge devices located in or around the arms. A leg band may be used to charges devices located in or around the legs.

A fully passive external power source is one which the patient, caregiver or physician need only set up once and then the patient charges their medical device simply by going about their daily routine.

An automatic turn-on feature automatically senses the proximity of the medical device to the external power source or to a primary coil associated with the external power source to commence energy transfer without intervention on the part of the patient. Such proximity sensing could take the form pressure sensing, heat sensing and/or metal sensing, as examples. Of course, other proximity sensing technologies could also be utilized.

Telemetry may be used to communicate device status to an implanted medical device, particularly to determine the status of the battery of an implanted medical device. In one example, telemetry could be used to terminate energy transfer when the battery of the implanted medical device has completely charging, i.e., is full. This further allows the external power source to be fully passive, without requiring patient intervention.

Various configurations of articles to physically associate either primary coils of the external power source or the external power source itself may be used.

In an embodiment, the article could be a pad that is placed on a bed for recharge while a patient is sleeping. This pad may be a thin pad that could be placed on top of bed sheets or below the sheets. This embodiment works well for a patient with a device in their back if they sleep on their back. Patients with devices located on their side may use this embodiment if they sleep on their sides. This bed pad embodiment does not need be an ambulatory solution and could be plugged into the wall. This provides a large power source for the application and allows charging of the device at larger distances than ambulatory devices. This means that a patient that tossed or turned during the night could still be charging the device even while moving.

In an embodiment, the article could be a blanket allowing patients to recharge their device by simply placing the blanket over their device. This allows patients with devices in their extremities to recharge during sleep. It also allows patients with devices in their stomach area to recharge while sleeping on their back. The blanket could also be non-ambulatory and could be plugged into the wall for as a power source. This power source allows larger charging distances and allows the patient to move with the blanket and not worry about the loss of recharge. The passive recharge blanket could double as a heating pad by having heating wires woven through it. If the blanket were already being plugged into the wall it would be easy to use some of that power for heating the wires placed in the blanket.

In an embodiment, the article could be a pad that would rest on the back of a chair. This pad could simply be placed on the back of a patient's chair so when they were seated in that chair they would automatically be charging. The pad is especially useful for patients with devices placed in hard to reach placed in their back. The pad may be placed on the seat of the chair for charging devices placed in the buttocks or back of the leg. The pad could also be non-ambulatory allowing the power source to be from the wall. Again, this allows larger charging distances and allows the patient to move slightly during the charging session.

In an embodiment, the article could be a chair paid placed, for example, on the back of an easy chair, especially a chair routinely sat in by the patient.

In an embodiment, the article could be placed on the seat of a car routinely used by the patient.

Figure 1:
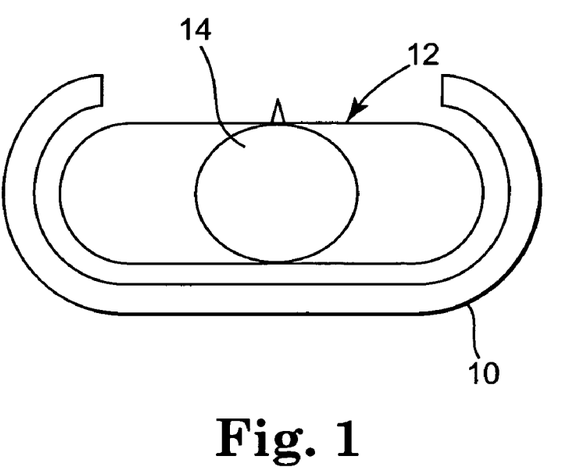
FIG. 1 illustrates a form factor for an external power source wrapping around a patient.

In an embodiment, the article could take the shape of contour around the patient's body as illustrated in FIG. 1. The article is a wrap-around pad 10 at least partially encompassing the abdomen 12 of patient 14. Pad 10 could take a number of shapes to fit the contours of a patient's body. For example, pad 10 could wrap around the patient's abdomen in a 180 degree manner as shown in FIG. 1.

Figure 2:
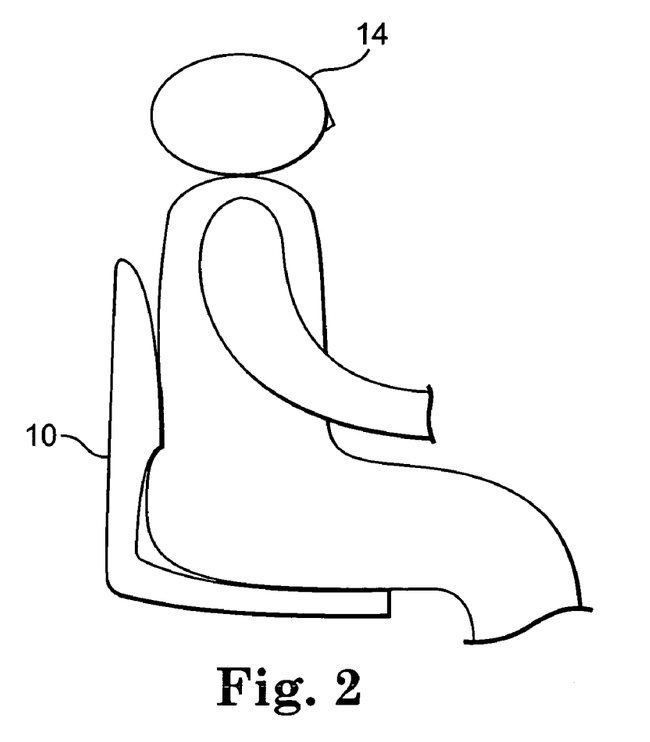
FIG. 2 illustrates a posterior shaped pad form factor for an external power source.

Alternatively, pad 10 could be designed to fit the posterior of patient 14 as illustrated in FIG. 2. In further embodiments, pad 10 could also be placed in a chair that was used by patient 14 for eating purposes. This allows patient 14 to recharge during breakfast, lunch and dinner and any other meals patient 14 might have. Still further, vibration could be included in pad 10 for comfort of patient 14. Since pad 14 generally is non-ambulatory, the power source for the vibrating feature would be from the wall and the vibration technology would be similar to that of commercially available vibrating chairs.

Figure 3:
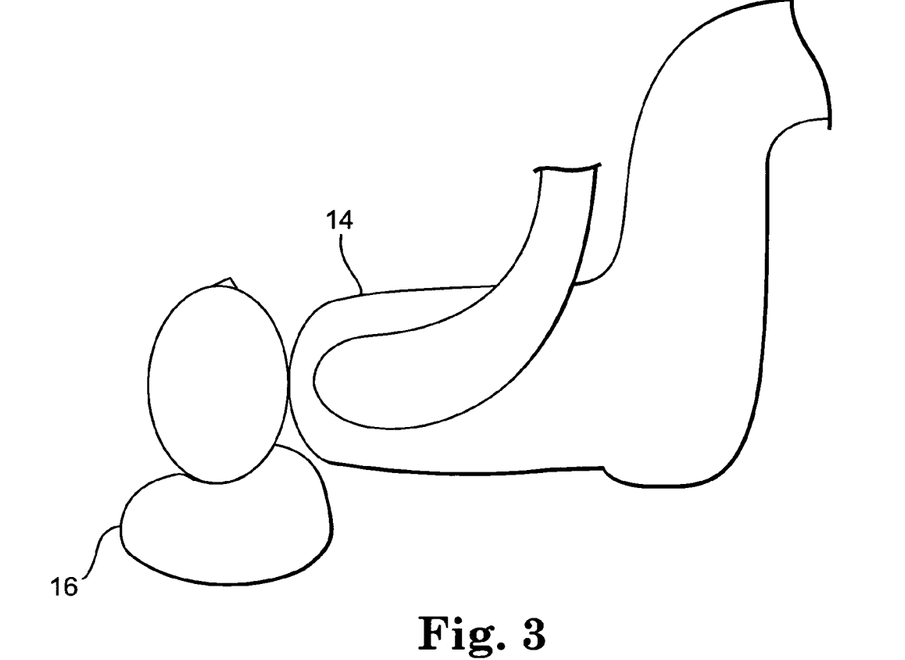
FIG. 3 illustrates a pillow form factor for an external power source.

In an embodiment, the article used for passive charging could be pillow 16 that patient 14 could rest their head on to charge or recharge as illustrated in FIG. 3. Pillow 16 allows patient 14 with a medical device placed in their head or neck to recharge passively while sleeping. Pillow 16 concept could be non-ambulatory and could be plugged into the wall. This allows significant charging distances and allows the patient to move without losing recharge.

Figure 4:
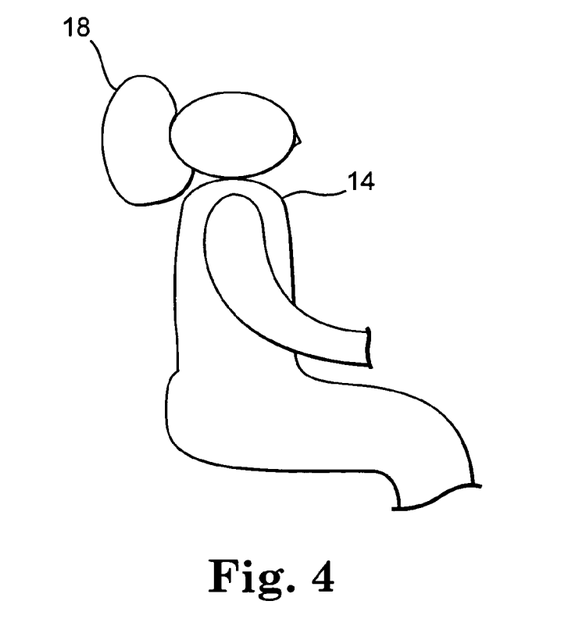
FIG. 4 illustrates a headrest form factor for an external power source.

In an embodiment, headrest 18, as illustrated in FIG. 4, could be placed on the back of a chair, on the headrest of a car seat, or any other place that patient 14 routinely rested their head. This allows patient 14 with a medical device placed in the head or neck to recharge passively while sitting upright or while lying down.

In an embodiment, passive charge or recharge could be accomplished in a recharge center for patient 14 to use in a follow-up visit to a medical clinic. There are some therapies that do not take large amounts of current and could simply be charged when patient 14 goes to a medical clinic for a follow-up appointment related to their medical device. Having passive recharge at follow-up would work well if the patient underwent routine follow-ups. Cardiac Rhythm management devices such as pacemakers and defibrillators consume low amounts of current compared to neurological therapies and could have significantly lengthy recharge intervals if they were to have rechargeable batteries. This means that the patients could recharge during their follow up visit to the clinic and not need to worry about charging in between visits to the clinic.

Primary coils associated with an external power source may contain a large number of small coils interconnected and packaged in a manner that allows patient 14 to use it every day. Packaging can help prevent damage to the external power source if it is spilled on. The packaging may also make the external power more comfortable for patient 14 to be in contact with every day and may provide greater longevity of the external power source.

Packaging used with external power source could ensure that the external power source is comfortable for patient 14 to use on a daily basis. There are a number of different materials that could be used to accomplish this such as simple cotton, but there are a few materials that would be optimal for some of the form factors.

Memory foam as is widely used for commercial pillow construction would give some consistency of location of primary coils and help maintain a minimal distance between the coils (the primary coils associated with the external power source and the secondary coils associated with the medical device. Memory foam would provide a soft, comfortable covering for these coils that would have some degree of capture.

Polar fleece could be used as a blanket and for a chair paid. Polar fleece would provide a soft, warm, and comfortable covering for the blanket and chair pad. Polar fleece can also be made fairly thin which allows the distance between the primary and secondary coils to be minimized.

A breathable fabric that wicks away moisture is one embodiment covering material for the clothing form factors. An example of this material would be the material that is produced by Under Armour. This material is comfortable when worn in direct contact to the skin. By wicking away moisture from the skin this allows this material to be comfortable while in direct contact with the skin for significant periods of time.

Figure 5:
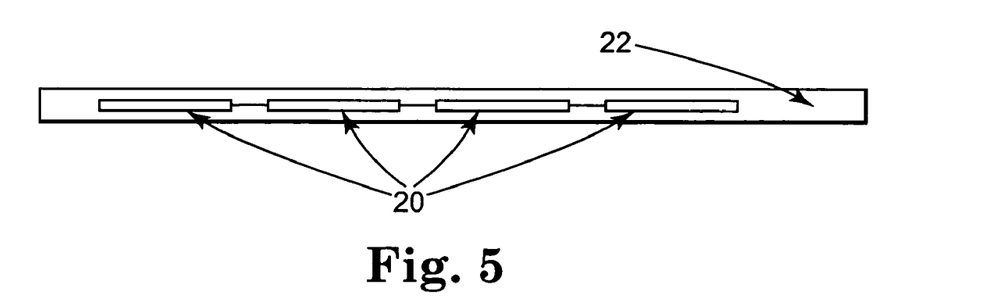
FIG. 5 illustrates a capturing of primary coils of external power source.

In certain form factors, primary coils 20 could be captured beneath a capturing material 22 to ensure that they are not damaged as illustrated in FIG. 5. This is especially the case for clothing form factors that will undergo stretching or bending forces and be more likely to get wet. Primary coils 20 could be over-molded with rubber. This would ensure flexibility but would hold primary coils 20 relative to one another. Rubber would also create a good moisture barrier to help prevent water damage to the external power source. Primary coils 20 may be packed in a gel. A gel could help the external power source form to the patient's body.

Electrical interconnect between the primary coils 20 should be able to handle significant amounts of flexing without breaking of the electrical connection. Cables of braided stranded wire could be used to interconnect primary coils 20. Braided stranded wire can handle significant amounts of flexing and provides a number of strands (so if one wire breaks there are many other wires still making the circuit). Primary coils 20 could also consist of helically wound coils that have excellent fatigue life and are used in cardiac leads that are flexed during every cardiac cycle. These primary coils 20 could be covered with some type of polymer, such as a Teflon™ type of polymer, to keep them safe. Also flex laminate substrate such as Kapton™ or FEP Teflon™ films may be used to carry traces of the interconnect material. This flexible substrate has been shown to handle many cycles of flexing and avoids or reduces damage to the interconnect.

Primary coils 20 may be of all sorts of sizes and shapes. The external power source could use a high amount of small coils. Using a high amount of small coils allows the external power source to power only a small number of coils that are directly over the medical device and allows form factors of the external power source to be highly flexible. Primary coils 20 may be 1" (2.54 centimeters) in diameter or less to ensure that the form factors are highly flexible.

Figure 6:
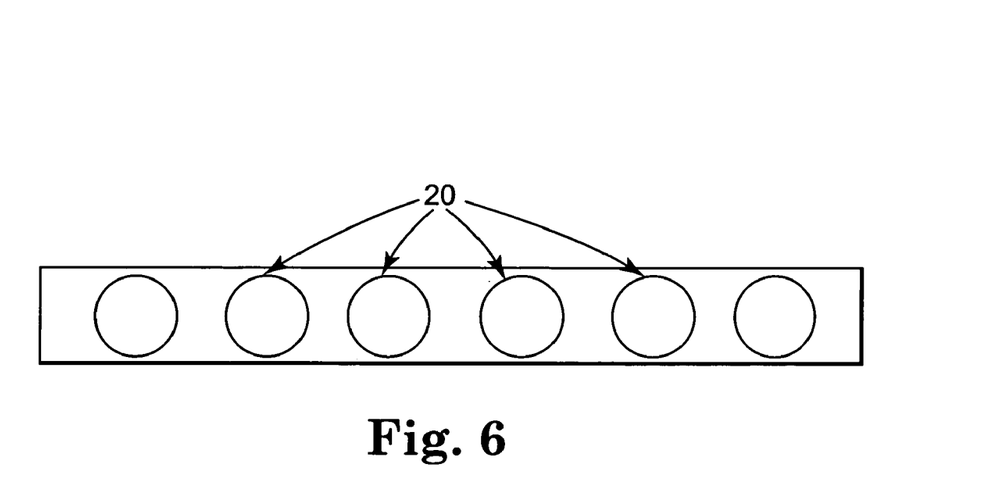
FIG. 6 illustrates an planar array of spherical primary coils.

Primary coils 20 could be shaped like spheres allowing primary coils 20 to be slightly closer to secondary coils of the medical device as shown in FIG. 6.

Figure 7:
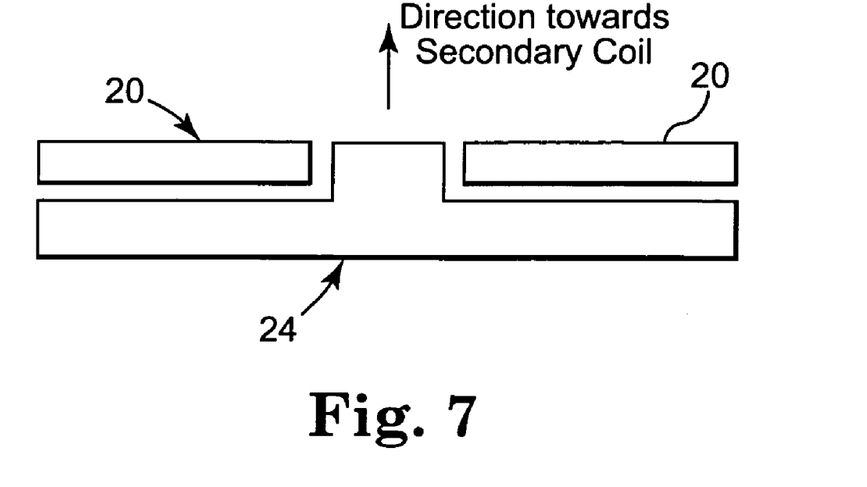
FIG. 7 illustrates use of a pot core in conjunction with a primary coil.

Pot cores 24 could be placed on the back side of each primary coil 20 to help focus the fields that are being created as illustrated in FIG. 7. Pot cores 24 could be made of materials such as manganese zinc.

Primary coils 20 could be constructed using wires having low impedance at high frequencies. For example, primary coils 20 may be constructed using Litz wire or magnet wire. This wire provides a benefit to charging because it has low impedance at high frequency. Primary coils 20 could be formed by lithography or any other etching processes. Primary coils 20 formed by lithography could be stacked and placed in series to created coils with higher numbers of turns than a single layer can provide. Primary coils 20 could be formed by pattern printing. Again, primary coils 20 formed by pattern printing could be stacked to create primary coils 20 with higher numbers of turns than a single layer can provide. Primary coils 20 may be made of a highly conductive material. Copper is an example of an inexpensive, highly conductive material. Other less conductive materials, such as MP35n may be used for better fatigue life and then can be plated with a more conductive material to bring the resistance per length down.

Figure 8:
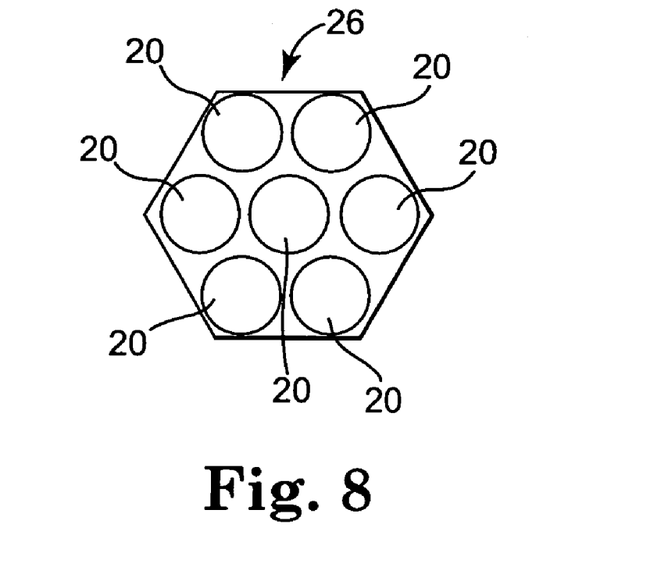
FIG. 8 illustrates a hexagonal array of primary coils.
Figure 9:
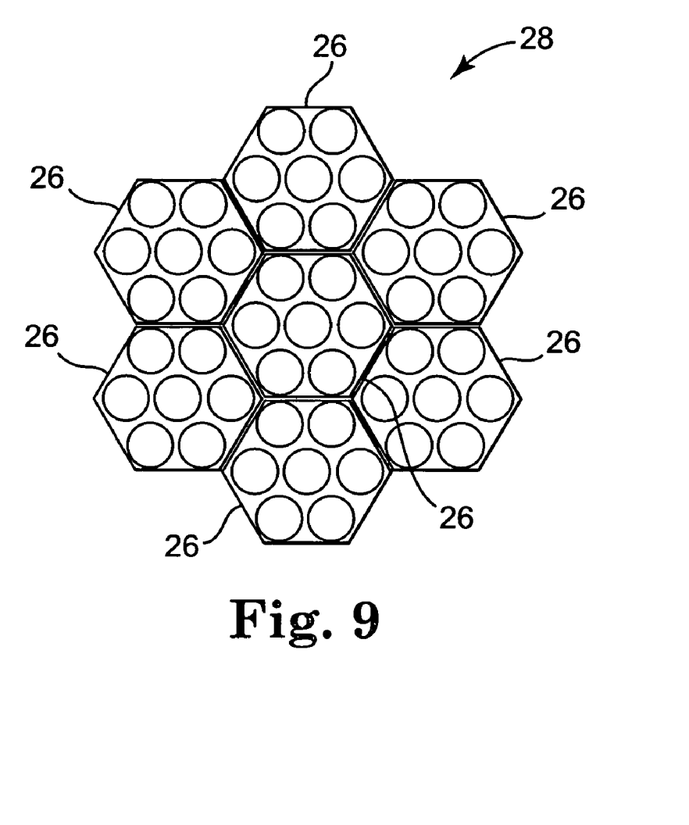
FIG. 9 illustrates a nested array of hexagonal arrays of primary coils.

Primary coils 20 may be set in a number of different configurations. First, primary coils 20 may be placed in a single plane. Primary coils could be positioned to form a hexagonal array 26 as shown in FIG. 8. Hexagonal arrays 26 may be repeated, or nested, to form an entire passive array 28 of primary coils 20 as illustrated in FIG. 9.

Figure 10:
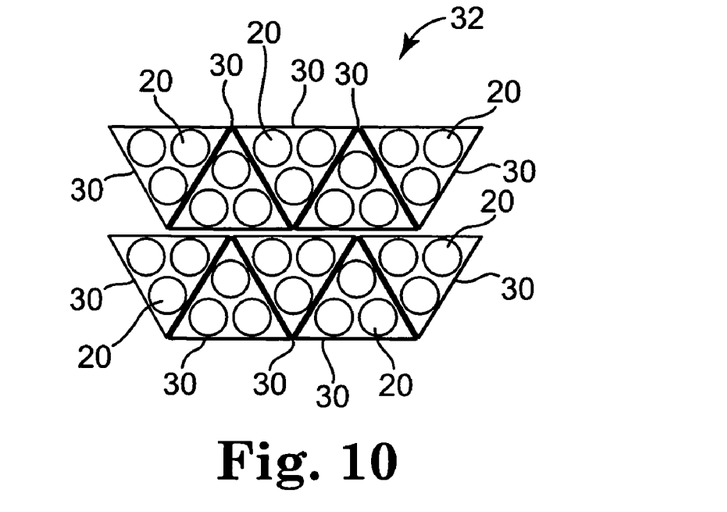
FIG. 10 illustrates a nested array of triangular arrays of primary coils.

Primary coils may be positioned in a triangular configuration whose triangles 30 may be repeated to form an array 32 of repeated triangles as illustrated in FIG. 10.

Figure 11:
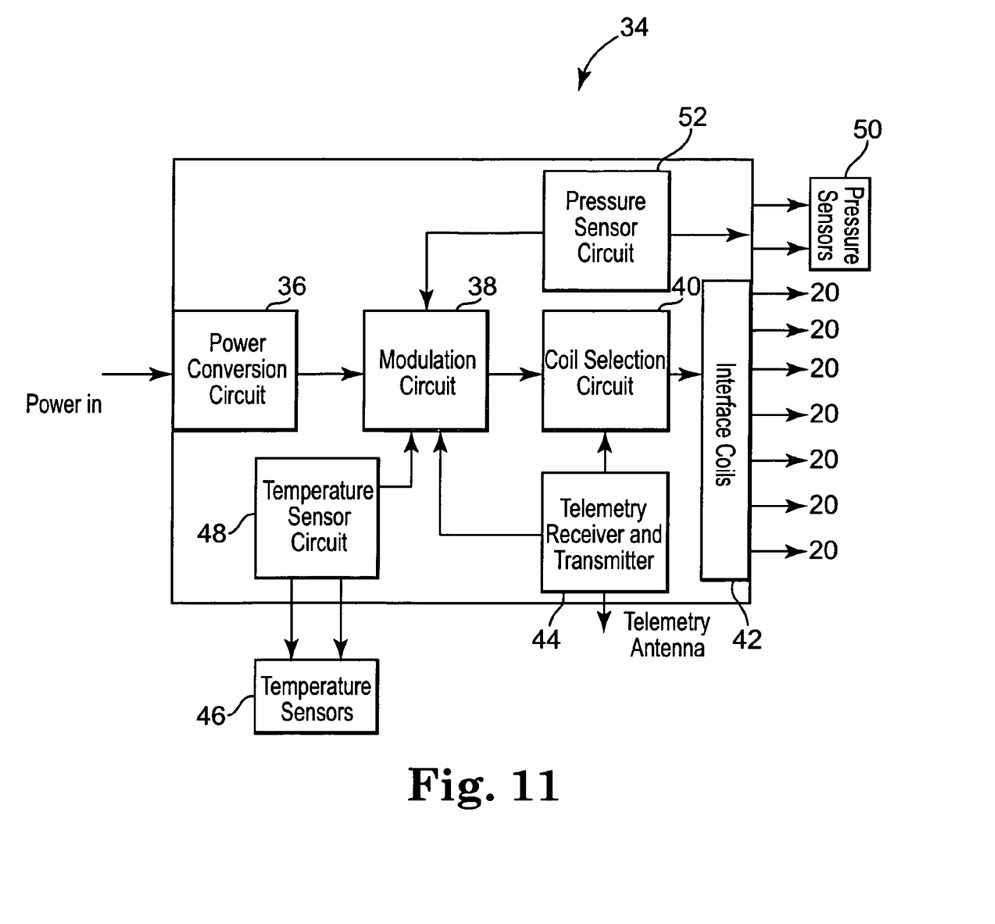
FIG. 11 is a block diagram of an external power source.

FIG. 11 illustrates a block diagram of electronics associated with the external power source 34.

External power source 34 may receive power from a wall power source or from a battery. In either case, a power conversion circuit 36 supplies appropriate power to modulation circuit 38.

The non-Ambulatory form factors (bed pad, pillow, blanket, and chair pad) allow external power source 34 to use line power. Patient 14 could simply plug external power source 34 into the wall and forget about it. Different plugs would be supplied for European patients.

The ambulatory form factors (clothes, bands) may require battery power for energy transfer. This could be accomplished using Li+ rechargeable batteries. Li+ batteries can be packaged in thin, flexible foil packs. These foil packs could be placed inside the ambulatory external power source 34. These batteries would have to be recharged and patient 14 could simply hang these clothes up on a special hanger to recharge them.

Modulation circuit 38 drives coil selection circuit 40 with a time-varying current enabling primary coils 20 coupled to coil selection circuit 40 through coil interface 42 to transmit energy through electromagnetic coupling.

Modulation circuit 38 is a frequency generator to generate a recharge signal, typically somewhere between 8 kiloHertz and 500 kiloHertz. The frequency of operation may depend on the form factor of external power source 34 or the variable frequency. External power source 34 could vary the frequency during a charging session to find the most optimal frequency for charging efficiency.

External power source 34 may have telemetry receiver and transmitter 44 enabling external power source 34 to in communication with an implanted medical device during a charging session. Telemetry receiver and transmitter 44 is conventional in nature and well known in the art. The implanted medical device could communicate battery status to the external power source. By knowing the battery status the external power source could stop charging when the battery of the implanted medical device was full.

It may not be possible to deliver recharge energy and telemeter to the implanted medical device at the same time so external power source 34 may have to stop sending recharge energy in order to poll the implanted medical device for information. A proximal telemetry system (5 centimeter communication distance) could be used for external power source 34 or an arm's length telemetry system could be used. Arm's length (~1 meter) telemetry can be achieved using E-field transmission (an example would be the MICS band set aside for medical device telemetry.) Arm's length telemetry (~1 meter) can also be achieved using H-field or coupled coil transmission.

External power source 34 could have an automatic turn-on sensor so patient 14 would not have to take any specific action to begin a charging session.

A temperature sensor 46 could be used to detect if patient 14 was in proximity to external power source 34. Temperature sensors 46 could be created using thermistors where the resistance changes with temperature. Temperature sensor circuit algorithm 48 receives signals from temperatures sensors 46 and alerts modulation circuit 38 to commence energy transfer upon representative of a temperature indicative of proximity of patient 14 to external power source 34 or to primary coils 20.

The charger could be automatically turned on using telemetry from the device. Telemetry could be used to automatically turn on external power source 34. External power source 34 could continuously send out requests for telemetry from the implanted medical device and when the implanted medical device was in proximity to the external power source 34, the implanted medical device would reply and external power source 34 could be turned on.

External power source 34 could include pressure sensors 50 to commence energy transfer. When patient 14 leans against a chair pad or lies down on a bed pad, pressure sensors 50 would detect the pressure. Pressure sensor circuit algorithm 52 would alert modulation circuit 38 and commence energy transfer.

Figure 12:
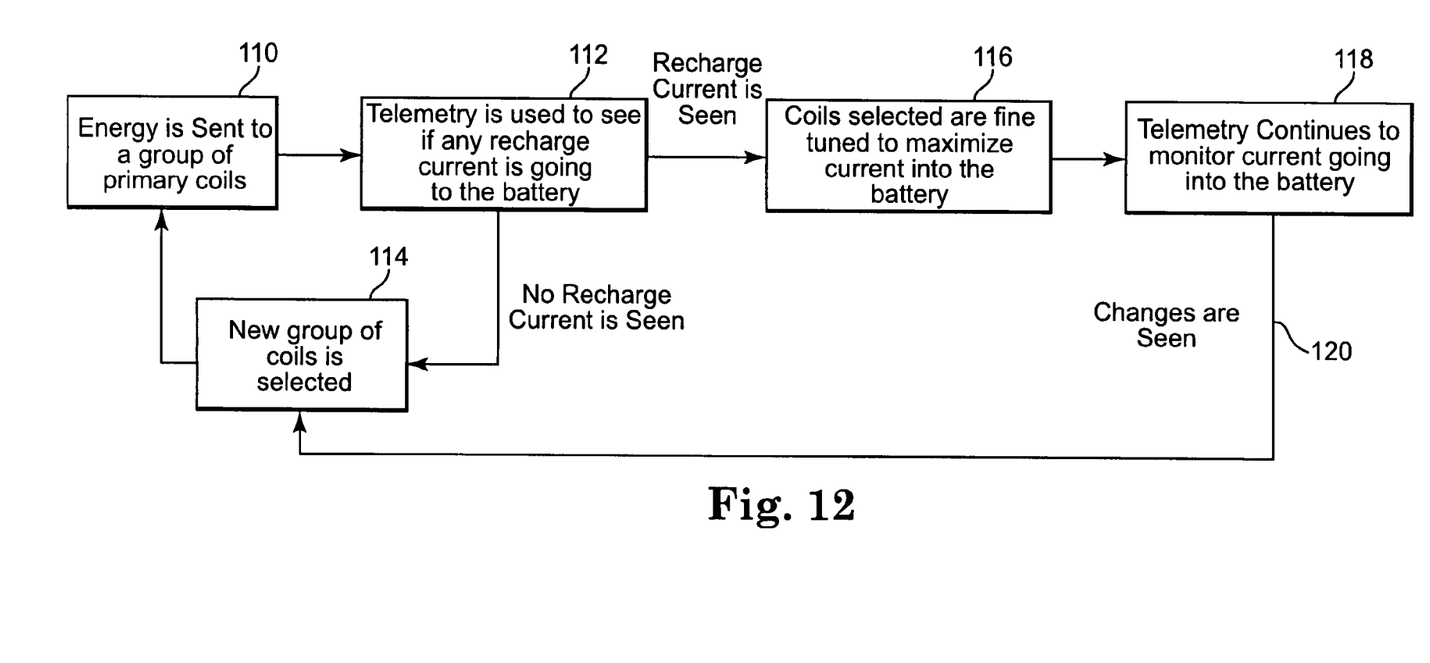
FIG. 12 is a flow chart of use of telemetry by external power source.

The implanted medical device could also communicate how much current was being put into the battery of the implanted medical device at any time. With this information, the external power source 34 could optimize the primary coils 20 that were being used to charge or the amount of power that each primary coil 20 as illustrated in FIG. 12.

Energy is sent (110) to a group of primary coils. Telemetry is used (112) to see if any charge or recharge current is going to the battery of the implanted medical device. If no recharge current is seen, a new group of primary coils 20 is selected (114) and the process returns to step 110. If recharge current is seen, primary coils 20 are fine tuned (116) to maximize current into the battery of the implanted medical device. Telemetry continues to monitor (118) current going into the battery of the implanted medical device. If changes in the current going into the battery of the implanted medical device are seen (120), a new group of primary coils 20 are selected (114) and the process repeats.

Temperature sensors 46 could also be used to ensure external power source was not getting too warm. Temperature sensors 46 could be used to detect if patient 14 was proximal to external power source 14 and could be used to monitor the temperature of external power source 14. It is generally accepted in the medical community that a temperature rise against the skin of patient 14 should not exceed 4 degrees Celsius to ensure that there is no damage to the tissue of patient 14. Temperature sensors 46 may be placed in a particular location or throughout external power source 34 to ensure that this temperature rise is not exceeded in a particular place or at any place on external power source 34.

A coil selection algorithm may be implemented in external power source 34 to help select which primary coils 20 should be powered at certain levels. It is feasible to have all of the primary coils 20 powered at all times, but selecting a certain subset of primary coils for higher power levels may increase the current delivered to the implanted medical device's battery and decrease the charging time.

Coil selection circuit 40 may use the resonant frequency of each of the primary coils 20. The resonant frequency of the primary coil 20 changes when the primary coil 20 is loaded by a secondary coil. If external power source 34 measures the resonant frequency of all of the primary coils 20 in external power source 34, external power source 34 could tell which primary coils 20 are in the closest proximity to the secondary coil. External power source 34 could then select which primary coils 20 to give the highest power.

Arm's length telemetry may also be used by coil selection circuit 40. external power source 34 could use arm's length telemetry to determine which primary coils 20 are closest to the secondary coil. External power source 34 could try powering different secondary coils 20 while communicating with the implanted medical device via arm's length telemetry to see which primary coils 20 cause the implanted medical device's battery to receive the most charge.

Short range telemetry could also be used by coil selection circuit 40 by having telemetry coils mixed in with primary coils 20 or using primary coils 20 to communicate with the implanted medical device by telemetry.

External power source 34 may automatically turn off when patient 14 has completed their charge or when patient 14 has left the proximity of external power source 34.

External power source 34 could find out when the implanted medical device's battery is full using short-range or arm's length telemetry. When the implanted medical device's battery is full it would simply send the signal via telemetry to external power source 34 that the battery was full and external power source 34 would stop transmitting recharge energy.

If external power source 34 has temperature sensors 46, external power source 34 could sense when patient 14 has left external power source 34 by looking at the temperature, typically a temperature decrease. If the temperature changes because patient 14 has left, external power source 34 could stop transmitting recharge energy.

If external power source 34 had pressure sensors 50 to check to see if patient 14 is using external power source 34, external power source 34 could sense when patient 14 left the external power source 34. When the pressure sensor 50 recognizes that patient 14 has left external power source 34, external power source 34 could stop transmitting recharge energy.

As noted above, energy transfer may cause external power source 34 to heat up. As discussed earlier, external power source 34 should preferably not have a temperature of more than four (4) degrees Celsius higher than skin of patient 14. External power source 34 may use water cooling, fan cooling, cooling with surface area radiant, refrigerator cooling or electrical cooling to ensure that external power source 34 heating is kept under control.

Thus, embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An external power source for an implantable medical device implantable in a patient, said implantable medical device having a secondary coil operatively coupled to therapeutic componentry, comprising:
   a power source;
   a modulation circuit operatively coupled to said power source;
   an article into which said patient may come into proximity;
   a plurality of primary coils operatively coupled to said modulation circuit and physically associated with said article;
   said modulation circuit driving at least one of said plurality of primary coils; and
   a sensor coupled to said modulation circuit and adapted to sense proximity of a component related to said implantable medical device;
   wherein said external power source automatically turns on and initiates a charging process without overt action by said patient;
   wherein said modulation circuit automatically commences operation to drive at least one of said plurality of primary coils when said sensor senses proximity with said component related to said implantable medical device.

2. The external power source as in claim 1 wherein said sensor comprises a pressure sensor and said proximity is sensed through weight of said patient on said article.

3. The external power source as in claim 1 wherein said sensor comprises a temperature sensor and said proximity is sensed through heat of said patient in proximity to said article.

4. The external power source as in claim 1 wherein said sensor comprises a metal detector and said proximity is sensed through proximity to said implantable medical device.

5. The external power source as in claim 1 which further comprises a coil selection circuit operatively coupled to said plurality of primary coils and to said modulation circuit, said coil selection circuit determining which of said plurality of primary coils are in closest proximity to said secondary coil of said implantable medical device, said modulation circuit driving those of said plurality of primary coils selected by said coil selection circuit.

6. The external power source as in claim 1 wherein said article comprises an article with which said patient routinely comes into proximity.

7. The external power source as in claim 6 wherein said article comprises a piece of furniture routinely used by said patient.

8. The external power source as in claim 7 wherein said article comprises a component of bedding utilized by said patient.

9. The external power source as in claim 8 wherein said article comprises a component of bedding selected from a group consisting of a mattress, mattress pad, sheet, blanket and pillow.

10. The external power source as in claim 6 wherein said article comprises an article of clothing worn by said patient.

11. An external power source for an implantable medical device implantable in a patient, said implantable medical device having a secondary coil operatively coupled to therapeutic componentry, comprising:
    a power source;
    a modulation circuit operatively coupled to said power source;
    an article into which said patient may come into proximity;
    a plurality of primary coils operatively coupled to said modulation circuit and physically associated with said article;
    said modulation circuit driving at least one of said plurality of primary coils; and
    a sensor coupled to said modulation circuit and adapted to sense proximity of a component related to said implantable medical device;
    wherein said external power source automatically turns on and initiates a charging process without overt action by said patient;
    wherein said modulation circuit commences operation to drive at least one of said plurality of primary coils when said sensor senses proximity with said component related to said implantable medical device; and
    wherein said modulation circuit ceases operation to drive at least one of said plurality of primary coils when said sensor ceases to sense proximity with said component related to said implantable medical device.

12. An external power source for an implantable medical device implantable in a patient, said implantable medical device having a secondary coil operatively coupled to therapeutic componentry, comprising:
    a power source;
    a modulation circuit operatively coupled to said power source;
    an article into which said patient may come into proximity;
    a plurality of primary coils operatively coupled to said modulation circuit and physically associated with said article;
    said modulation circuit driving at least one of said plurality of primary coils; and
    a sensor coupled to said modulation circuit and adapted to sense proximity of a component related to said implantable medical device;
    wherein said external power source automatically turns on and initiates a charging process without overt action by said patient in response to sensing proximity of said component related to said implantable medical device;
    wherein said modulation circuit commences operation to drive at least one of said plurality of primary coils when said sensor senses proximity with said component related to said implantable medical device; and
    wherein said implantable medical device has a rechargeable power source operatively coupled to said therapeutic componentry wherein said external power source recharges said rechargeable power through said secondary coil when driven by at least one of said plurality of primary coils.

13. The external power source as in claim 12 wherein said rechargeable power source comprises a rechargeable battery.

14. A method of externally powering an implantable medical device implantable in a patient, said implantable medical device having a secondary coil operatively coupled to therapeutic componentry, comprising the steps of:
    sensing proximity of a component related to said implantable medical device; and
    turning on an external power source and initiating a charging process in response to said sensing step without overt action by said patient;
    physically associating a plurality of primary coils operatively with an article into which said patient may come into proximity;

modulating at least one of said plurality of primary coils with said external power source;

automatically commencing operation to drive at least one of said plurality of primary coils when said sensing step senses proximity with said component related to said implantable medical device.

15. The method as in claim 14 further comprising the step of ceasing operation to drive at least one of said plurality of primary coils when said sensing step ceases to sense proximity with said component related to said implantable medical device.

16. The method as in claim 14 wherein said sensing step comprises detecting a pressure through weight of said patient on said article.

17. The method as in claim 14 wherein said sensing step comprises sensing heat of said patient in proximity to said article.

18. The method as in claim 14 wherein said sensing step comprises detecting metal through proximity to said implantable medical device.

19. The method as in claim 14 further comprising the step of determining which ones of said plurality of primary coils are in closest proximity to said secondary coil of said medical device and selectively modulating said ones of said plurality of primary coils.

20. The method as in claim 14 wherein said article comprises an article with which said patient routinely comes into proximity.

21. The method as in claim 20 wherein said article comprises a piece of furniture routinely used by said patient.

22. The method as in claim 21 wherein said article comprises a component of bedding utilized by said patient.

23. The method as in claim 22 wherein said article comprises a component of bedding selected from a group consisting of a mattress, mattress pad, sheet, blanket and pillow.

24. The method as in claim 20 wherein said article comprises an article of clothing worn by said patient.

* * * * *

UNITED STATES PATENT AND TRADEMARK OFFICE
CERTIFICATE OF CORRECTION

| | | |
|---|---|---|
| PATENT NO. | : 7,650,192 B2 | Page 1 of 1 |
| APPLICATION NO. | : 11/414136 | |
| DATED | : January 19, 2010 | |
| INVENTOR(S) | : Carl D. Wahlstrand | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 538 days.

Signed and Sealed this

Twenty-third Day of November, 2010

David J. Kappos
*Director of the United States Patent and Trademark Office*